United States Patent
Powell et al.

(12) 
(10) Patent No.: US 6,660,892 B2
(45) Date of Patent: Dec. 9, 2003

(54) SYNTHESIS OF ALIPHATIC 1,3-DIOLS UTILIZING REDUCED LIGAND CONCENTRATION AND WATER EXTRACTION

(75) Inventors: Joseph Broun Powell, Houston, TX (US); Paul Richard Weider, Houston, TX (US); John Frederick Knifton, Houston, TX (US); Kevin Dale Allen, Prairieville, LA (US); Lynn Henry Slaugh, Houston, TX (US); Juan Pedro Arhancet, Creve Coeur, MO (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/360,302

(22) Filed: Feb. 7, 2003

(65) Prior Publication Data

US 2003/0166977 A1 Sep. 4, 2003

Related U.S. Application Data (60) Provisional application No. 60/356,601, filed on Feb. 13, 2002.

(51) Int. Cl.[7] .......................... C07C 27/00; C07C 29/00
(52) U.S. Cl. ...................... 568/867; 568/327; 568/451; 568/861; 568/862; 568/909; 562/152; 562/153; 562/154; 562/155; 562/162; 556/13; 556/16; 556/20; 556/138
(58) Field of Search ................... 568/867, 862, 568/861, 866, 909, 451, 327; 502/153, 152, 154, 155, 162; 556/13, 16, 20, 138

(56) References Cited

U.S. PATENT DOCUMENTS

| | | | |
|---|---|---|---|
| 5,304,691 A | 4/1994 | Arhancet et al. | ........... 568/867 |
| 5,770,776 A | 6/1998 | Powell et al. | ............... 568/862 |
| 5,777,182 A | 7/1998 | Powell et al. | ............... 568/862 |
| 6,469,222 B2 | 10/2002 | Knifton et al. | ............. 568/867 |

*Primary Examiner*—Johann Richter
*Assistant Examiner*—Elvis O. Price
(74) *Attorney, Agent, or Firm*—Donald F. Haas (57) ABSTRACT

This invention is a process for synthesizing aliphatic 1,3-diols in one step by hydroformylation and hydrogenation of oxirane, carbon monoxide, and hydrogen employing a catalyst comprising a cobalt carbonyl compound and a cocatalyst metal compound ligated with a ligand in a ligand to cocatalyst metal atom molar ratio in the range of 0.2:1.0 to 0.6:1.0, optionally in the presence of a promoter, where recovery of product is preferably accomplished via water extraction of a diol rich phase from the bulk reaction mixture. The process modifications can, particularly in combination, be beneficial with respect to product recovery, catalyst recycle, and overall economics of a one-step process for producing aliphatic 1,3-diols.

32 Claims, 2 Drawing Sheets

SYNTHESIS OF ALIPHATIC 1,3-DIOLS UTILIZING REDUCED LIGAND CONCENTRATION AND WATER EXTRACTION

This application claims the benefit of U.S. Provisional Application No. 60/356,601 filed Feb. 13, 2002, the entire disclosure of which is hereby incorporated by reference.

FIELD OF THE INVENTION

This invention relates to the hydroformylation and hydrogenation synthesis of an aliphatic 1,3-diol, particularly 1,3-propanediol, from an oxirane, especially ethylene oxide (hereafter EO), and syngas in one step using a catalyst system comprised of cobalt carbonyl and a ligand.

BACKGROUND OF THE INVENTION

Aliphatic 1,3-diols, particularly 1,3-propanediol, have many applications as monomer units for polyester and polyurethane, and as starting materials for the synthesis of cyclic compounds. For example, CORTERRA® polytrimethylene terephthalate is a polyester characterized by outstanding properties that is made of 1,3-propanediol (hereafter PDO) and terephthalic acid. There is much interest in the art in finding new routes for synthesizing PDO that are efficient, economical, and demonstrate process advantages.

U.S. Pat. Nos. 3,463,819 and 3,456,017 teach the hydroformylation of ethylene oxide to produce 1,3-propanediol and 3-hydroxypropanal (hereafter HPA) using a tertiary phosphine-modified cobalt carbonyl catalyst. U.S. Pat. Nos. 5,256,827; 5,344,993; 5,459,299; 5,463,144; 5,463,145; 5,463,146; 5,545,765; 5,545,766; 5,545,767; and, 5,563,302, 5,689,016, all assigned to Shell Oil Company, disclose cobalt catalyzed hydroformylation of ethylene oxide.

U.S. Pat. No. 5,304,691, assigned to Shell Oil Company, discloses a method of hydroformylating ethylene oxide to 3-hydroxypropanal and 1,3-propanediol in a single step using an improved catalyst system comprising a cobalt-tertiary phosphine ligand in combination with a ruthenium catalyst. In '691 PDO and HPA are produced by intimately contacting an oxirane, particularly ethylene oxide (EO), a ditertiary phosphine-modified cobalt carbonyl catalyst, a ruthenium co-catalyst, and syngas (carbon monoxide and hydrogen) in an inert reaction solvent at hydroformylation reaction conditions. A PDO yield of up to 86–87 mole % is reported, using a catalyst comprising cobalt ligated with 1,2-bis (9-phosphabicyclononyl) ethane as bidentate ligand, and either triruthenium (0) dodecacarbonyl or bis[ruthenium tricarbonyl dichloride] as cocatalyst. Also see U.S. Pat. No. 5,304,686, assigned to Shell, which discloses the synthesis of 3-hydroxypropanal using a ditertiary phosphine-modified cobalt carbonyl catalyst and a catalyst promoter. In the aforementioned patents, where a phosphine ligand is employed, it is bound to cobalt carbonyl.

It is known that water extraction can recover HPA intermediate or PDO product from an non-water-soluble solvent system in a two-step process and that use of a lipophilic promoter (quaternary ammonium or phosphonium, or lipophilic amine) rather than a sodium salt allows a majority of the cobalt carbonyl catalyst to recycle with the organic solvent phase, as desired. See, for example, U.S. Pat. Nos. 5,463,144; 5,463,145; 5,463,146; 5,545,765; 5,545,766; 5,545,767; 5,563,302; 5,576,471; 5,585,528; 5,684,214; 5,689,016; 5,731,478; 5,723,389; 5,770,776; 5,777,182; 5,786,524; and 5,841,003, all assigned to Shell.

Copending commonly assigned U.S. patent application Ser. Nos. 09/808,974 and 09/963,068 disclose, inter alia, phosphine ligated bimetallic catalyst compositions useful in the one-step synthesis of PDO, and a process for one-step synthesis of PDO. In these references the phosphine ligands are bound to the ruthenium compound rather than the cobalt compound.

Ruthenium carbonyls modified with phosphine ligands are quite effective as catalyst complexes in the one-step synthesis of PDO. However, phosphine ligands are relatively expensive and, in some cases, catalyst recycle may fall short of optimal. At the same time, product selectivity may fall short upon repeated recycle. These observations have thus far made it rather prohibitive to use phosphine ligands in hydroformylation catalysts for commercial use. It would be extremely desirable if substantially less ligand were effective in a bimetallic catalyst complex for the one-step synthesis of PDO and if other modifications, such as water extraction, enhanced the use of a reduced ratio and contributed to efficient recycle.

SUMMARY

In accordance with the foregoing, the present invention is a process for hydroformylating and hydrogenating oxiranes, especially ethylene oxide, carbon monoxide, and hydrogen to produce aliphatic 1,3-diols, especially PDO, in one step where recovery of product is accomplished via aqueous extraction, preferably with water, of a diol rich phase from the bulk reaction liquor. The preferred process comprises the steps of:

(a) Contacting at a temperature within the range from about 30 to about 150° C. and a pressure within the range of about 3 to about 25 MPa, an oxirane, particularly ethylene oxide, carbon monoxide, and hydrogen, in an essentially non-water-miscible solvent in the presence of an effective amount of a homogeneous bimetallic hydroformylation catalyst comprising a cobalt carbonyl compound, preferably an essentially non-ligated cobalt carbonyl compound, and a cocatalyst metal, which is selected from ruthenium, copper, platinum, and palladium, and which is ligated with a ligand selected from a phosphine ligand, a bidentate or multidentate N-heterocyclic ligand, a porphorine ligand, and a phospholanoalkane ligand, optionally in the presence of a promoter, preferably a lipophilic promoter, wherein the molar ratio of ligand to cocatalyst metal atom may vary from about 0.2:1.0 to about 0.6:1.0, preferably about 0.20:1.0 to about 0.40:1.0, under reaction conditions effective to produce a reaction product mixture containing an aliphatic 1,3-diol such as PDO;

(b) Adding an aqueous liquid to said reaction product mixture and extracting into said aqueous liquid a major portion of the 1,3-diol (PDO) at a temperature less than about 100° C. to provide an aqueous phase comprising the 1,3-diol (PDO) in greater concentration than the concentration of 1,3-diol (PDO) in the reaction product mixture and an organic phase comprising at least a portion of the bimetallic hydroformylation catalyst and preferably any promoter;

(c) Separating the aqueous phase from the organic phase; and (d) Optionally but preferably returning at least a portion of the organic phase containing catalyst to step (a).

This invention relates to modifications of said one-step process for synthesizing aliphatic 1,3-diols, especially PDO, which comprise: a) employing 4- to 5-fold less ligand at lower ligand/cocatalyst metal ratios than previously thought effective; and b) employing water extraction to recover product and recycle catalyst. These modifications offer a significant economic advantage, as the use of reduced ligand offers the potential to substantially reduce ligand usage and cost, while water extraction allows recycle of a majority of catalyst with the solvent phase with -reduced thermal degradation.

DETAILED DESCRIPTION OF THE INVENTION

In the present invention we have discovered several process modifications that can, particularly in combination, be beneficial with respect to product recovery, catalyst recycle, and overall economics of a one-step hydroformylation and hydrogenation process for producing aliphatic 1,3-diols, especially PDO, using a cobalt:cocatalyst metal-:ligand hydroformylation catalyst. We have found that extracting the product with water and employing a cobalt-:cocatalyst metal:ligand catalyst system having a lower concentration of ligand than previously believed to be effective is advantageous in the one-step synthesis of aliphatic 1,3-diols. The reduced ligand catalyst system can reduce process costs by both minimizing the amount of ligand exposed to process conditions and by preferentially placing the ligand in what is possibly a more stable configuration, i.e. bound to the cocatalyst metal which preferably is ruthenium. Extraction with water optimizes recycle of catalyst and enhances catalyst stability. The liquid extraction does not entail thermal stress of high cost catalyst components, and, hence, is an advantageous method for recycle of catalyst during commercial production of high boiling products such as 1,3-propanediol.

In the process of the present invention, oxiranes of up to 10 carbon atoms, preferably up to 6 carbon atoms, and ethylene oxide (EO) in particular, may be converted into their corresponding 1,3-diols by the hydroformylation reaction with syngas in the presence of a hydroformylation catalyst complex having a reduced ratio of cocatalyst metal:ligand, as will be described below.

The 1,3-diols are made by charging the oxirane, catalyst, and/or catalyst promoter, and reaction solvent to a pressure reactor with the introduction of syngas (a mixture of hydrogen and carbon monoxide, suitably in a molar ratio of about 1:1 to about 8:1, preferably about 2:1 to about 6:1) under hydroformylation conditions.

The process of the present invention may be operated as a batch-type process, continuous process, or mixed forms thereof, however the features of the present invention would permit a continuous one-step process to operate more effectively and efficiently than previously possible. The invention process can be carried out in the continuous mode in a homogeneous reaction mixture. The reaction conditions which permit this mode of operation include use of a moderate polarity solvent or solvent blend, (described below), and an oxirane concentration in the reaction mixture of at least about 0.1 wt %. Reaction in 2 to 4 reactors with staged oxirane (EO) addition is preferred for continuous operation.

The one-step reaction process includes conversion of the oxirane EO to PDO via intermediate 3-hydroxypropanal, which is formed and hydrogenated to PDO in-situ. By "in-situ" in this context is meant that conversion of ethylene oxide to PDO is carried out without isolation of the intermediate 3-hydroxypropanal and in the presence of a single catalyst system for both hydroformylation and hydrogenation. The reaction is carried out under conditions effective to produce a reaction product mixture containing PDO with relatively minor amounts of 3-hydroxypropanal (3-HPA), acetaldehyde, and heavy ends (materials which are less volatile than the desired product). The following description of the process will specifically highlight PDO but the process description is intended to be descriptive of processes to make other aliphatic 1,3-diols as well.

For best results, the process is conducted under conditions of elevated temperature and pressure. Reaction temperatures range from ambient temperature, preferably about 30° C., to about 150° C., preferably from about 50 to about 125° C., and most preferably from about 60 to about 110° C. The reaction pressure (total pressure, or partial pressure if inert gaseous diluents are used) is desirably in the range from about 3 to about 25 MPa, preferably from about 5 to about 15 MPa, most preferably from about 7 to about 12 MPa. In a batch process, the reaction will generally be complete within about 1.5 to about 5 hours.

Figure 1:
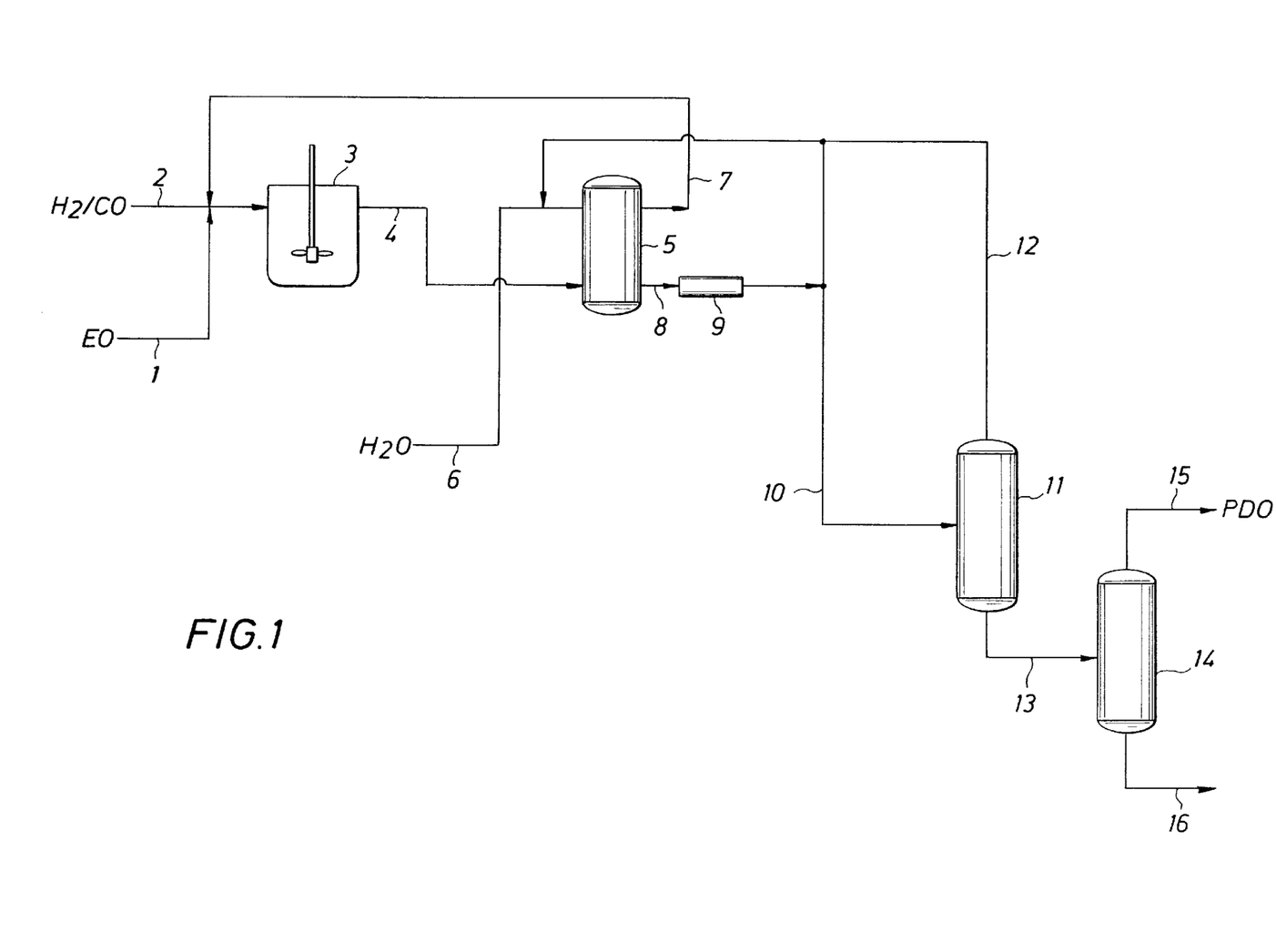
FIG. 1 is a schematic drawing of the process of the present invention.
Figure 2:
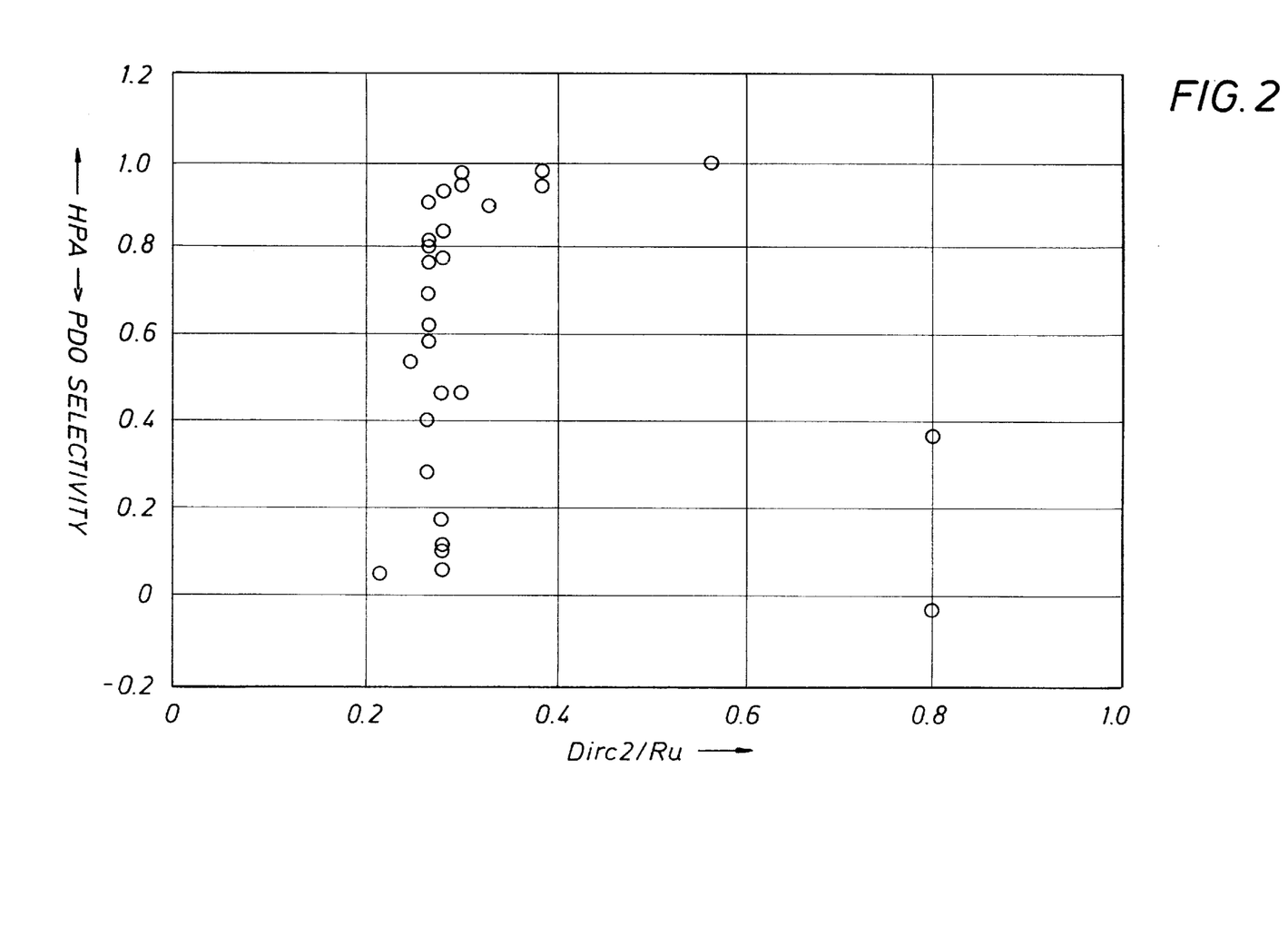
FIG. 2 is a graph showing a plot of HPA to PDO conversion versus ligand/Ru ratio.

The one-step 1,3-propanediol preparation process of the present invention can be conveniently described by reference to FIG. 1. Separate or combined streams of ethylene oxide 1, carbon monoxide and hydrogen 2 are charged to hydroformylation vessel 3, which can be a pressure reaction vessel such as a bubble column or agitated tank, operated batchwise or in a continuous manner. The feed streams are contacted in the presence of the dilute ligand bimetallic catalyst of the present invention.

Following the hydroformylation reaction, the hydroformylation reaction product mixture 4 containing PDO and HPA, the reaction solvent, the bimetallic catalyst, and a minor amount of other reaction products, is passed to extraction vessel 5, to which an aqueous liquid, generally water, and optional miscibilizing solvent, are added via 6 for extraction and concentration of the PDO. Liquid extraction can be effected by any suitable means, such as mixer-settlers, packed or trayed extraction columns or rotating disk contactors. Extraction can if desired be carried out in multiple stages. The water-containing hydroformylation reaction product mixture can be passed to a settling tank (not shown) for resolution into aqueous and organic phases.

The amount of water added to the hydroformylation reaction product mixture will generally be such as to provide a water:mixture ratio within the range of about 1:1 to about 1:20, preferably about 1:1 to about 1:10, most preferably about 1:5. The addition of water at this stage of the reaction may have the additional advantage of suppressing formation of undesirable heavy ends. Extraction with a relatively small amount of water provides an aqueous phase that is greater than about 10 wt % PDO, preferably greater than about 20 wt % PDO.

The water extraction is preferably carried out at a temperature within the range of about 5 to about 90° C., most preferably about 25 to about 55° C., with higher temperatures avoided to minimize condensation products (heavy ends) and catalyst decomposition. In order to maximize catalyst recovery, it is preferred to perform the water extraction under a minimum of about 0.3 to about 5 MPa, preferably about 0.3 to about 1.2 MPa, of carbon monoxide at about 25° C. to about 55° C. The carbon monoxide may be present as the partial pressure of a total gas mixture containing other components, such as mixtures with hydrogen as used for the reaction step.

The organic phase containing the reaction solvent and the major portion of the bimetallic catalyst can be recycled from the extraction vessel to the hydroformylation reaction via 7. Aqueous extract 8 is optionally passed through one or more acid ion exchange resin beds 9 for removal of any catalyst present. An optional post hydrogenation step may be conducted to complete the total reversion of aldehyde intermediate to diol, if desired.

The extractant water 10 can be recovered by distillation in column 11 and recycled to the water extraction process via a further distillation (not shown) for separation and purge of light ends. The PDO-containing stream 13 can be passed to one or more distillation columns 14 for recovery of PDO 15 from heavy ends 16.

The one-step hydroformylation and hydrogenation reaction is carried out in a liquid solvent inert to the reactants. By "inert" is meant that the solvent is not consumed during the course of the reaction. In general, ideal solvents will solubilize carbon monoxide, will be essentially non-water-miscible and will exhibit low to moderate polarity such that the PDO will be solubilized to the desired concentration of about 5 wt % under hydroformylation conditions, while significant solvent will remain as a separate phase upon water extraction. By "essentially non-water-miscible" is meant that the solvent has solubility in water at about 25° C. of less than about 25 wt % so as to form a separate hydrocarbon-rich phase upon water extraction of PDO from the hydroformylation reaction mixture. Preferably this solubility is less than about 10 wt %, most preferably less than about 5 wt %. The solubilization of carbon monoxide in the selected solvent will generally be greater than about 0.15 v/v (1 atm, 25° C.), preferably greater than about 0.25 v/v, expressed in terms of Ostwald coefficients.

Suitable solvents are described in U.S. Pat. No. 5,304,691 incorporated herewith by reference in the entirety. Good results may be achieved with ethers, including cyclic and acyclic ethers, optionally in combination with an alcohol or aromatic hydrocarbon.

One group of suitable reaction solvents is alcohols and ethers that can be described by the formula:

Where $R_1$ is hydrogen or $C_{1-20}$ linear, branched, cyclic, or aromatic hydrocarbyl or mono- or polyalkylene oxide and $R_2$ is $C_{1-20}$ linear, branched, cyclic or aromatic hydrocarbyl, alkoxy or mono- or polyalkylene oxide.

Preferred reaction solvents can be described by the formula:

In which $R_1$ is hydrogen or $C_{1-8}$ hydrocarbyl and $R_3$, $R_4$, and $R_5$ are independently selected from $C_{1-8}$ hydrocarbyl, alkoxy, or alkylene oxide. Such ethers include, for example, methyl-t-butyl ether, ethyl-t-butyl ether, diethyl ether, phenylisobutyl ether, ethoxyethyl ether, diphenyl ether, and diisopropyl ether, particularly methyl-t-butyl ether.

It is generally preferred to regulate the concentration of water in the hydroformylation reaction mixture, as excessive amounts of water reduce PDO selectivity below acceptable levels and may induce formation of a second liquid phase. Acceptable water levels will depend upon the solvent used, with more polar solvents generally more tolerant of higher water concentrations. For example, optimum water levels for hydroformylation in methyl-t-butyl ether solvent are believed to be within the range of about 1 to about 2.5 wt %. Water concentrations are to a large degree set by the solubility of water in the solvent, as introduced for the extraction step.

The oxirane (EO) concentration is maintained at a low level to minimize unselective side reactions. Oxiranes will preferably be maintained throughout the reaction in a concentration not less than about 0.2% by weight, generally within the range of about 0.2 to about 20% by weight, preferably about 1 to about 10% by weight, based on the total weight of the reaction. The process of the invention can be carried out in a continuous mode, while maintaining said EO concentration, by staged EO addition, for example.

Catalysts useful in the one-step process scheme of the present invention include certain homogeneous bimetallic catalysts comprising a cobalt carbonyl compound and a cocatalyst metal component, preferably a ruthenium, copper, platinum, or palladium compound, ligated with a ligand selected from a phosphine ligand, a bidentate or multidentate N-heterocyclic ligand, a porphorine ligand, or a phospholanoalkane ligand. The molar ratio of ligand to cocatalyst metal atom may vary from about 0.2:1.0 to about 0.6:1.0, preferably about 0.20:1.0 to about 0.40:1.0. Higher ligand ratios may be employed to reduce formation of light ends byproducts, but result in increased process costs.

Suitable cobalt sources also include salts that are reduced to the zero valence state by heat-treatment in an atmosphere of hydrogen and carbon monoxide. Sufficient cobalt (0) should be added to completely oxidize all of the complexed cocatalyst metal employed. An excess of cobalt can be added, but is not of particular value. Suitably, the cocatalyst metal to cobalt molar ratio can be as low as 0.05:1.0, preferably 0.1:1.0, and generally varies from about 4:1 to about 1:4, preferably from about 2:1 to about 1:3, more preferably from about 1:1 to about 1:2. Examples of such salts comprise, for example, cobalt carboxylates such as acetates, octanoates, etc., which are preferred, as well as cobalt salts of mineral acids such as chlorides, fluorides, sulfates, sulfonates, etc. Cobalt oxide or hydroxide may be fed as a slurry. Operable also is mixtures of these cobalt salts. The reduction may be performed prior to the use of the catalysts, or it may be accomplished simultaneously with the hydroformylation process in the hydroformylation zone.

The amount of cobalt present in the reaction mixture will vary depending upon the other reaction conditions, but will generally fall within the range of about 0.01 to about 1 wt %, preferably about 0.05 to about 0.3 wt %, based on the weight of the reaction mixture.

The oxidation state of the cocatalyst metal atom is not entirely certain (for example, in theory ruthenium may have a valence of 0 to 8 which may even change during the course of the hydroformylation reaction). Accordingly, the molar ratio of cocatalyst metal to cobalt may vary within relatively broad ranges. Suitable cocatalyst metal sources include, but are not limited to, carbonyls, oxides, carboxylates, and metal. Examples include triruthenium dodecacarbonyl and ruthenium (IV) oxide.

The cobalt component may be ligated with the same ligand that is in the cocatalyst metal ligand or with a different ligand. The preferred catalysts comprise a mostly (essentially), preferably completely, non-ligated cobalt component and ligated cocatalyst metal compound. These catalyst complexes can be identified by signature absorption peaks on an infrared spectrum of the catalyst composition. The cocatalyst metal may be ligated with a diphosphine ligand, as discussed in copending U.S. patent application Ser. No. 09/808,974, a multidentate or bidentate N-heterocyclic ligand as discussed in copending U.S. patent application Ser. No. 60/291,826, or a class of bis (phospholano) alkane ligands as discussed in U.S. patent application Ser. No. 60/295,769.

The tertiary diphosphine phosphorus ligand is of the general formula:

RRP—Q—PR'R' wherein each group R and R' independently or jointly is a hydrocarbon moiety of up to 30 carbon atoms, and Q is an organic bridging group of 2 to 4 atoms in length. The group R or R', when monovalent, may be alkyl, cycloalkyl, bicycloalkyl or aryl, and preferably of up to 20 carbon atoms, more preferably of up to 12 carbon atoms. Alkyl and/or cycloalkyl groups are preferred. The group Q is preferably composed of carbon atoms, which may form part of a ring system such as a benzene ring or a cyclohexane ring. More preferably Q is an alkylene group of 2, 3 or 4 carbon atoms in length, most preferably of 2 carbon atoms in length. A non-limiting list of illustrative diphosphines of this class includes 1,2-bis (dimethylphosphino)ethane; 1,2-bis (diethylphosphino)ethane; 1,2-bis (diisobutylphosphino) ethane (BDIBPE); 1,2-bis(dicyclohexylphosphino) ethane; 1,2-bis(2,4,4-trimethylpentylphosphino)ethane; 1,2-bis (diethylphosphino)propane; 1,3-bis(diethylphosphino) propane; 1-(diethylphosphino)-3-(dibutylphosphino) propane, 1,2-bis(diphenylphosphino)ethane; 1,2-bis (dicyclohexylphosphino)ethane; 1,2-bis(2-pyridyl, phenylphosphanyl)benzene; 1,2-bis (dicyclopentyphosphino)ethane; 1,3-bis(2,4,4-trimethylpentyphosphino)propane; 1,2-bis (diphenylphosphino) benzene, and the like. These groups R and R' may be substituted with non-hydrocarbon groups themselves. Both groups R and/or both groups R' may also form a ring with the phosphorus atom(s), such as a phosphacycloalkane of from 5 to 8 atoms. Examples on 5-ring systems (phospholano-based ligands) include 1,2-bis (phospholano)ethane, 1,2-bis (2,5-dimethylphospholano) benzene, optically pure (R, R), (R, S), (S, S) 1,2-bis(2,5-dimethylphospholano)ethane or its racemic mixture, and the like. The ring itself may be part of a multiring system. Examples of such ring systems may be found in the aforementioned '691 patent and in WO-A-9842717, incorporated by reference herein in the entirety. In the former phosphabicyclononyl groups are described, in the latter adamantyl-like groups and phosphatrioxatricyclodecyl groups in particular are described. Diphosphines wherein both groups R and R' form a ring with the phosphorus atom are preferred. The most preferred ligands are 1,2-P, P'-bis (9-phosphabicyclo [3.3.1] and/or [4.2.1](nonyl) ethane (hereinafter B9PBN-2), its 1,2-P, P'-propane and/or its 1,3-P,P'-propane analogue (hereinafter B9PBN-3).

Ditertiary phosphine ligands are commercially available. Catalysts prepared therefrom are known in the art and their method of preparation is described in detail in U.S. Pat. Nos. 3,401,204 and 3,527,818, which are both incorporated by reference herein in the entirety. The phosphine ligands may also be partially oxidized to phosphine oxides in the manner described in the '691 patent.

When ligating the ruthenium, the preferred cocatalyst metal, with a diphosphine ligand, for example, it is hypothesized that the result is a tertiary diphosphine ruthenium tricarbonyl compound, but it might also be a bis (tertiary diphosphine ruthenium) pentacarbonyl compound. Unligated ruthenium carbonyl is believed to be an inactive species, and the catalyst preparation therefore seeks to ligate each ruthenium atom.

Where the ligand is a N-heterocyclic, a large number of N-heterocyclic compounds have been identified as suitable ligands for the one-step PDO synthesis using the cobalt-ruthenium catalyst couple. Suitable types of bidentate and multidentate N-heterocyclic ligands include, but are not limited to: iazines such as pyrimidine, pyrazine, pyridazine, as well as benzodiazines such as quinazoline and quinoxaline; bispyridines such as 2,2'-dipyridyl (DIPY), 2,2'-bipyrimidine (BPYM), 1,10-phenanthroline (PHEN), di-2-pyridyl ketone, 4,4'-dimethyl-2, 2'-dipyridyl, 5,6-dimethylphenanthroline, 4,7-dimethylphenanthroline, 2,2'-biquinoline, neocuproine, and 2,2'-dipyridylamine; multipyridines such as 2,4,6-tripyridyl-s-triazine (TPTZ), 3,6-di-2-pyridyl-1,2,4,5-tetrazine, 2,2':6',2"-terpyridine, 2,3-bis(pyridyl)pyrazine, and 3-(2-pyridyl)-5,6-diphenyl-1, 2,4-triazine; pyridine, 3-hydroxypyridine, and quinoline, particularly the lower cost homologues derived from coal-tar extracts; and certain 2,6-pyridyl-diimines such as 2,6-bis(N-phenyl, methylimino)pyridine and 2,6-bis[N-(2,6-diisopropylphenyl)methylimino]pyridine.

Preferred heterocyclic compounds for use as ligands include 2,2'-dipyridyl (DIPY), 2,2'-bipyrimidine (BPYM), and 2,4,6-tripyridyl-s-triazine (TPTZ). The structures of these three N-heterocyclics are as follows:

In the case where ruthenium is ligated with a phospholanoalkane, suitable phospholanoalkanes include phospholane substituted alkane compounds of formula II and I as follows:

where, in both Formula I and II, R is a lower alkyl, trifluoromethyl, phenyl, substituted phenyl, aralkyl, or ring-substituted aralkyl; and n is an integer from 1 to 12; and for formula II, A is $CCH_3$ CH, N or P. Preferred are compounds of formula I and II wherein R is a lower alkyl of $C_1$ to $C_6$ alkyl and n is 1 to 3. Most preferred are those compounds of formula I and II wherein R is methyl and n is 1 to 3.

Examples of such compounds include, but are not limited to, 1,2-bis(phospholano) ethane, 1,2-bis(2,5-dimethylphospholano)ethane, 1,2-bis [(2R, 5R)-2,5-dimethylphospholano]ethane; 1,2-bis [(2S, 5S)-2,5-dimethylphospholano]ethane; 1,3-bis(2,5-dimethylphospholano)propane; tris [(2,5-dimethylphospholano)methyl]methane; tris [(2,5-dimethylphospholano)ethyl]amine; or 1,1,1-tris [(2,5-dimethylphospholano)ethyl]ethane. Particularly useful are bidentate, bis(phospholano)alkanes such as, for example, 1,2-bis [(2R, 5R)-2,5-dimethylphospholano]ethane (BDMPE), 1,2-bis [(2S, 5S)-2,5-dimethylphospholano] ethane, a racemic mixture of the two, plus 1,2 bis (phospholano)ethane.

Porphorine ligands generally comprise four pyrrole-type ring moieties, arranged in a cyclic structure, that may optionally also incorporate various alkyl and aryl substituents both on the pyrrole rings and on the connecting methine groups. Suitable porphorine ligands in the practice of this invention include octaethylporphorines and tetraphenylporphorines, as well as the closely related phthalocyanines.

Generally the preferred counter ion is believed to be cobalt tetracarbonyl ($[Co(CO)_4]^-$), although the ion in the active catalyst may be a modification thereof. Part of the cobalt compound may be modified with (excess) tertiary diphosphine, e.g., up to about 75 mole %, preferably up to about 50 mole %. However, the counter ion is preferably the non-ligated cobalt tetracarbonyl. Cobalt carbonyls can be generated by reaction of a starting cobalt source such as cobalt hydroxide with syngas, as described in J. Falbe, "Carbon Monoxide in Organic Synthesis", Springer-Verlag, NY (1970), for example.

The catalysts may be prepared by the stepwise method, which is preferred, or the self-assembly method, both of which are discussed briefly below and described in more detail in U.S. Pat. No. 6,469,222, which is herein incorporated by reference. In the preferred embodiment of this invention, the conditions and, in particular, the solvent, are selected such as to favor the formation of a ligated ruthenium, copper, platinum, or palladium species, rather than a ligated cobalt species.

In the stepwise method, the ligated cocatalyst metal component is prepared first, and then the cobalt carbonyl component and any promoter are added to the cocatalyst metal complex solution. For example, a ruthenium complex is formed by reaction of a ruthenium carbonyl such as triruthenium dodecacarbonyl with a stoichiometric amount of the selected ligand. The reaction is carried out in a solvent in which any catalyst intermediates are soluble. The solution is heated to a temperature within the range of about 90 to about 130° C., preferably about 100 to about 110° C., under a carbon monoxide atmosphere, for a time sufficient for complete reaction of the ligand with the ruthenium, usually about 1 to about 3 hours. The selected cobalt carbonyl and any promoter used are then added to the solution of ligated ruthenium carbonyl and the solution is maintained at the elevated temperature for a time of about 15 to about 60 minutes.

In the self-assembly method, careful selection of the catalyst precursors and the catalyst preparation solvent are important in obtaining the desired final catalyst composition. It is necessary for the ligand to react with the cocatalyst metal compound prior to the generation of any cobalt (0) carbonyl by reduction. Self-assembly catalyst preparation is carried out by combining, in a solvent, a cobalt salt such as cobalt octanoate, a cocatalyst metal compound such as a ruthenium (0) carbonyl such as triruthenium dodecacarbonyl, and a ligand for the cocatalyst metal. The starting ingredients are present in a Co:cocatalyst metal ratio within the range of about 1:0.15 to about 1:2, preferably about 1:2, and a ligand:cocatalyst metal atom ratio within the range of about 0.2:1.0 to about 0.6:1.0, preferably about 0.2:1.0 to about 0.4:1.0. The solution is heated at a temperature within the range of about 110 to about 130° C. under a reducing atmosphere such as 1:4 $CO:H_2$ for a time effective for essentially complete ligation of the cocatalyst metal, generally about 1 to about 3 hours. Table 2 includes data comparing the stepwise and self-assembly methods in the context of the present invention.

Whether generated by stepwise or self-assembly, the preferred bimetallic catalysts exhibit specific signature infrared bands, as discussed in U.S. Pat. No. 6,469,222. The presence of the cocatalyst metal-ligated species rather than the Co-ligated species may be confirmed by, e.g., IR analysis.

The optimum ratio of oxirane feed to bimetallic catalyst complex will in part depend upon the particular complex employed. However, molar ratios of oxirane to the cobalt within the catalyst complex from about 2:1 to about 10,000:1 are generally satisfactory, with molar ratios of from about 50:1 to about 500:1 being preferred.

The hydroformylation reaction mixture optionally, and preferably, will include a catalyst promoter to accelerate the reaction rate. Suitable promoters include sources of mono- and multivalent metal cations of weak bases such as alkali, alkaline earth and rare earth metal salts of carboxylic acids. Also suitable are lipophilic promoters such as lipophilic phosphonium salts and lipophilic amines, which accelerate the rate of hydroformylation without imparting hydrophilicity (water solubility) to the active catalyst. By "lipophilic" is meant that the promoter tends to remain in the organic phase after extraction of PDO with water. The promoter will generally be present in an amount within the range of about 0.01 to about 0.6 moles per mole of cobalt.

Any alkali metal salt that is at least partially soluble in the reaction mixture is suitable. Both inorganic salts and organic salts of alkali metals are suitable. Included in the inorganic salts are halides, chromates, sulfates, borates, carbonates, bicarbonates, chlorates, phosphates, etc. Particularly desirable organic salts are salts or carboxylic acids having carbon numbers ranging from 1 to about 20. Examples of alkali metal salts that have been found suitable include sodium bromide, sodium iodide, potassium iodide, sodium borate, lithium acetate, potassium acetate, cesium acetate, and particularly sodium acetate.

Lipophilic compounds may include, but not be limited to, quaternary ammonium or phosphonium salts, lipophilic amines, or arsine, and lipophilic phosphine oxide. Suitable quaternary ammonium salts include those represented by the formula:

in which each R group is independently selected from unsubstituted and inertly substituted $C_{1-25}$ linear, branched, cyclic or aromatic hydrocarbyl, alkoxy or mono-polyalkylene oxide, and A is a basic anion having a conjugate acid of pKa>2 such as carboxylate, phenate and hydroxide, for example. A is not halide. Two or more of the R groups together may form a cyclic or aromatic structure. Such quaternary ammonium salts include benzyltributylammonium acetate, benzyltrimethylammonium methoxide, benzyltrimethylammonium hydroxide and ethoxylated quaternary ammonium salts such as those available under the trade name Ethoquad®. A quaternary ammonium salt that is convenient to use due to its availability and demonstrated promotion of ethylene oxide hydroformylation is benzyltributyl ammonium acetate.

Suitable lipophilic phosphine oxides include those represented by the formula:

in which each R group is independently selected from unsubstituted and inertly substituted $C_{1-25}$ linear, branched, cyclic and aromatic hydrocarbyl and mono- and polyalkylene oxide. Such phosphine oxides include triphenylphosphine oxide, tributylphosphine oxide, dimethylphenylphosphine oxide, and triethylphosphine oxide. Triphenylphosphine oxide is particularly useful.

Suitable lipophilic arsines include those represented by the formula:

In which each of $R_1$, $R_2$, and $R_3$ is independently selected from unsubstituted and inertly substituted $C_{1-25}$ linear, branched, cyclic and aromatic hydrocarbyl, alkoxy or mono- or polyalkylene oxide. Two or more of the R groups together may form a cyclic or aromatic structure. Such arsines include triphenylarsine and triethylarsine.

Suitable lipophilic promoters also include tertiary amines such as nonylpyridine and dimethyldodecylamine; lipophilic phosphonium salts such as tetrabutylphosphonium acetate; lipophilic ammonium salts such as quaternary ammonium acetate; and lipophilic dihydroxyarenes such as hydroquinone. Dimethyldodecylamine was used with good results in the examples summarized in Table 3.

Optimum commercial operation will require efficient dilute ligand catalyst recovery with essentially complete recycle of catalyst to the hydroformylation reaction. The catalyst recovery process may involve two or more steps, beginning with the above-described water extraction of PDO under carbon monoxide from the hydroformylation product mixture. The organic phase can be recycled to the hydroformylation reactor, with optional purge of heavy ends. That portion of the catalyst which remains with the aqueous product phase may be recovered and recycled via an alternate separation scheme, including thermal separation (distillation). Use of ligand in the catalyst formulation decreases the volatility of catalyst components, allowing recycle with the bottoms phase from thermal recovery separations such as distillation or evaporation.

The following examples will serve to illustrate the invention disclosed herein. The examples are intended only as a means of illustration and should not be construed as limiting the scope of the invention in any way. Those skilled in the art will recognize many variations that may be made without departing from the spirit of the disclosed invention.

EXPERIMENTAL

EXAMPLES 1–42

Batch one-step syntheses of 1,3-propanediol (PDO) from ethylene oxide (EO) and syngas (CO, $H_2$) were conducted in a 300-ml stirred autoclave with stirred draft-tube gas dispersion to insure excellent gas-liquid mass transfer. Reaction mixtures were prepared in an $O_2$-free glove box using $O_2$-free solvents and chemicals. Preparation entailed weighing between 0.05 and 2 grams of dicobaltoctacarbonyl, triruthenium dodecacarbonyl, a catalyst ligand (e.g. bidentate phosphine or amine), a reaction promoter (e.g. sodium acetate), and solvent, or solvent mixture as needed to bring the total reaction mass to 150 grams. Mixtures were added to the stainless steel autoclave body, capped with Teflon® stopper, and transported out of the glove box to the reactor assembly.

The fixed reactor head was purged with nitrogen. A separate nitrogen line was connected to the reactor body containing the air sensitive reaction mixture, such that upon removing the stopper, the body and head could be connected under flowing nitrogen, to exclude air. The sealed assembly was then depressured and pressured three times with nitrogen to remove any residual oxygen. The appropriate syngas ratio for reaction was then established by pressuring the reactor with a target amount of $H_2$, followed by pressuring with a syngas (CO and $H_2$) blend of the desired composition. Since a "one step" synthesis of PDO from EO was desired, a 2:1 ratio of $H_2$/CO was desired as synthesis gas, to provide for additional "make up" syngas of the correct stoichiometric composition:

Hydroformylation: EO+$H_2$+CO →3-HPA

Hydrogenation: 3-HPA+$H_2$→1,3-PDO where "3-HPA" is the 3-hydroxypropanal intermediate formed via EO hydroformylation. Thus, by adding makeup syngas of the same ratio as that consumed by the overall reaction, a constant $H_2$/CO syngas ratio could be maintained.

The reaction mixture was first heated to the desired reaction temperature (typically 60–100° C.) under 7 to 12 MPa of syngas, to preform the desired catalyst species prior to introduction of EO reactant. Typically 30 minutes were allowed for preforming. The reaction apparatus was equipped with a pressurized sight glass filled via transfer from a small cylinder (0.5 kg capacity) equipped with dip tube to allow transfer of 5–50 grams of ethylene oxide to the sight glass, for measured dosing into the autoclave reactor. A nitrogen pressure of 0.5 to 1.5 MPa was maintained on the EO cylinder, and the sight glass apparatus was prepressured with a minimum of 0.3 MPa of nitrogen, such that EO was transferred under a protective blanket of $N_2$, to avoid regimes which would allow explosive self-decomposition. Concentrations of EO in the final reaction mixture were limited to less than 15 weight percent, to avoid regimes where explosive decomposition could occur at reaction temperatures.

Syngas was used to pressure the EO from the sight glass into the reactor to initiate a reaction run. Upon addition of EO, syngas was consumed per the hydroformylation and hydrogenation reactions described above. The corresponding decrease in pressure vs. time was logged via a pressure transmitter and recording device. As the pressure diminished from 12 to 8 MPa, the reactor was manually refilled with syngas. The reaction was assumed complete when pressure uptake diminished to negligible rates.

The reactor was fitted with a dip tube which allowed liquid samples to be taken at designated intervals. Approximately 3 to 5 grams of sample were purged through the dip tube assembly in order to obtain a sample representative of the stirred reactor contents. Samples could be collected directly in an infrared cell for off-line analysis of catalyst species. These species were found to be sufficiently stable to allow analysis within 30 minutes of sampling. Alternatively, the liquid sample was carefully throttled through an internal standard solution chilled to zero degrees centigrade to trap unconverted EO. This sample was shot on a temperature programmed capillary gas chromatograph equipped with flame ionization detector for analysis of unreacted EO, 3-HPA intermediate, PDO product, and acetaldehyde/ethanol byproducts. Separate liquid samples were analyzed by atomic spectroscopy to confirm cobalt, ruthenium, and ligand (P, N) concentrations.

The entire assembly was housed in a hood to prevent personnel exposure to ethylene oxide and carbon monoxide. A CO detector and fire eye provided monitoring and protection. An electrically heated jacket provided temperature control for the reactor. Automated overtemperature shut downs were included for a thermocouple in the reactor jacket. A rupture disk or EO-compatible pressure relief valve was employed to protect the reactor and assembly against overpressure. Table 1 shows the final concentrations of catalyst components tested via preparations in this manner. Table 2 shows a dilute ligand comparison of the self-assembly and stepwise preform method.

MTBE=methyl-t-butylether
DPE=diphenylether
TBA=t-butyl alcohol

TABLE 1

Batch Dilute Ligand One-Step PDO Synthesis via Self-Assembly

| Example | Promoter/Co | Ru/Co | Ligand/Ru | Solvent | Co Wt % | Preform T (° C.) | Reaction T (° C.) | $H_2$/CO | Reaction rate G/L/Hr | Final PDO + HPA % | PDO + HPA Selectivity | Conv. HPA → PDO |
|---|---|---|---|---|---|---|---|---|---|---|---|---|
| 1 | 0.30 | 0.40 | 0.39 | 30% THF/MTBE | 0.10 | 80 | 80 | 5 | 35 | 16.02 | 0.71 | 0.98 |
| 2 | 0.30 | 0.40 | 0.39 | 30% THF/MTBE | 0.10 | 80 | 80 | 5 | 33 | 11.49 | 0.68 | 0.95 |
| 3 | 0.30 | 0.20 | 0.33 | 30% THF/MTBE | 0.20 | 80 | 80 | 5 | 22 | 11.52 | 0.66 | 0.90 |
| 4 | 0.70 | 0.60 | 0.27 | 30% TBA/MTBE | 0.10 | 80 | 80 | 5 | 25 | 13.00 | 0.65 | 0.81 |
| 5 | 0.70 | 0.60 | 0.27 | 30% TBA/MTBE | 0.10 | 80 | 80 | 5 | 56 | 11.95 | NM | 0.82 |
| 6 | 0.70 | 0.60 | 0.27 | 30% TBA/MTBE | 0.10 | 80 | 80 | 5 | 67 | 6.74 | NM | 0.59 |
| 7 | 0.30 | 0.30 | 0.22 | 30% MTBE/THF | 0.20 | 80 | 80 | 2 | 169 | 11.65 | 0.85 | 0.06 |
| 8 | 0.70 | 0.55 | 0.28 | 30% TBA/MTBE | 0.10 | 80 | 80 | 5 | 34 | 14.67 | 0.82 | 0.96 |
| 9 | 0.70 | 0.55 | 0.28 | 30% TBA/MTBE | 0.10 | 80 | 80 | 5 | 38 | 9.45 | 0.71 | 0.85 |
| 10 | 0.70 | 0.55 | 0.28 | 30% TBA/MTBE | 0.10 | 80 | 80 | 5 | 40 | 4.60 | 0.58 | 0.12 |
| 11 | 0.70 | 0.55 | 0.28 | MTBE | 0.10 | 80 | 80 | 5 | 23 | 11.40 | 0.57 | 0.94 |
| 12 | 0.70 | 0.55 | 0.28 | MTBE | 0.10 | 80 | 80 | 5 | 45 | 10.40 | 0.84 | 0.83 |
| 13 | 0.70 | 0.55 | 0.28 | MTBE | 0.10 | 80 | 80 | 5 | 17 | 4.85 | 0.55 | 0.78 |
| 14 | 0.70 | 0.55 | 0.28 | MTBE | 0.10 | 80 | 80 | 5 | 35 | 3.61 | 0.40 | 0.47 |
| 15 | 0.30 | 0.30 | 0.28 | MTBE | 0.20 | 90 | 90 | 5 | 40 | 6.91 | 0.38 | 0.78 |
| 16* | | | | | | | | | | | | |
| 17 | 0.00 | 0.55 | 0.56 | MTBE | 0.05 | 80 | 80 | 5 | 10 | 7.68 | 0.85 | 0.99 |
| 18 | 0.00 | 0.55 | 0.56 | MTBE | 0.05 | 80 | 80 | 5 | 13 | 4.57 | 0.89 | 0.92 |
| 19 | 0.70 | 0.60 | 0.27 | MTBE | 0.10 | 70 | 75 | 5 | 15 | 7.98 | 0.65 | 0.91 |
| 20 | 0.70 | 0.60 | 0.27 | MTBE | 0.10 | 70 | 75 | 5 | 24 | 7.01 | 0.68 | 0.77 |
| 21 | 0.70 | 0.60 | 0.27 | MTBE | 0.10 | 70 | 75 | 5 | 40 | 4.63 | 0.78 | 0.29 |
| 22 | 0.70 | 0.60 | 0.25 | MTBE | 0.10 | 80 | 80 | 5 | 24 | 12.41 | 0.67 | 0.95 |
| 23 | 0.70 | 0.60 | 0.25 | MTBE | 0.10 | 80 | 80 | 5 | 47 | 9.03 | 0.64 | 0.54 |
| 24 | 0.33 | 0.30 | 0.28 | MTBE | 0.20 | 90 | 90 | 4 | 50 | 9.62 | 0.48 | 0.02 |
| 25 | 0.33 | 0.30 | 0.28 | MTBE | 0.20 | 90 | 90 | 4 | 203 | 7.00 | 0.78 | 0.36 |
| 26 | 0.33 | 0.30 | 0.28 | 30% DPE/THF | 0.20 | 80 | 135 | 2 | 4 | 1.49 | 0.11 | 0.85 |
| 27 | 0.67 | 1.00 | 0.30 | MTBE | 0.05 | 80 | 80 | 5 | 21 | 8.06 | 0.68 | 0.98 |
| 28 | 0.67 | 1.00 | 0.30 | MTBE | 0.05 | 80 | 80 | 5 | 23 | 5.95 | 0.78 | 0.95 |
| 29 | 0.67 | 1.00 | 0.30 | MTBE | 0.05 | 80 | 80 | 5 | 36 | 4.08 | 0.89 | 0.47 |
| 30 | 0.00 | 0.30 | 0.28 | MTBE | 0.10 | 80 | 80 | 5 | 34 | 9.75 | 0.58 | 0.18 |
| 31 | 0.00 | 0.30 | 0.28 | MTBE | 0.10 | 80 | 80 | 5 | 44 | 8.94 | 0.80 | 0.11 |
| 32 | 0.00 | 0.30 | 0.28 | MTBE | 0.10 | 80 | 80 | 5 | 50 | 5.04 | 0.70 | 0.06 |
| 33 | 0.70 | 0.60 | 0.27 | .1 PDO/.3 TBA/.6 MTBE | 0.10 | 80 | 80 | 2 | 10 | 5.19 | 0.26 | 0.63 |
| 34 | 0.70 | 0.60 | 0.27 | .1 PDO/.3 TBA/.6 MTBE | 0.10 | 80 | 80 | 2 | 43 | 11.34 | 0.83 | 0.74 |
| 35* | | | | | | | | | | | | |
| 36 | 0.30 | 0.30 | 0.33 | .1 PDO (1:1 MTBE/THF) | 0.20 | 80 | 80 | 5 | 3 | 1.16 | 0.62 | 0.85 |
| 37 | 0.67 | 0.60 | 0.80 | .1 PDO 1:1 MTBE/TBA | 0.10 | 80 | 80 | 5 | 14 | 4.50 | 0.24 | 0.00 |

TABLE 1-continued

Batch Dilute Ligand One-Step PDO Synthesis via Self-Assembly

| Example | Promoter/ Co | Ru/ Co | Ligand/ Ru | Solvent | Co Wt % | Preform T (° C.) | Reaction T (° C.) | H$_2$/ CO | Reaction rate G/L/Hr | Final PDO + HPA % | PDO + HPA Selectivity | Conv. HPA → PDO |
|---|---|---|---|---|---|---|---|---|---|---|---|---|
| 38 | 0.67 | 0.60 | 0.80 | .1 PDO 1:1 MTBE/TBA | 0.10 | 80 | 80 | 5 | 46 | 7.96 | 0.53 | 0.36 |
| 39 | 0.67 | 0.60 | 0.80 | .1 PDO 1:1 MTBE/TBA | 0.10 | 80 | 80 | 5 | 35 | 4.00 | 0.37 | 0.47 |
| 40 | 0.67 | 0.60 | 0.27 | 10% PDO/MTBE | 0.10 | 80 | 80 | 5 | 21 | 9.10 | 0.48 | 0.62 |
| 41 | 0.67 | 0.60 | 0.27 | 10% PDO/MTBE | 0.10 | 80 | 80 | 5 | 31 | 6.72 | 0.59 | 0.70 |
| 42 | 0.67 | 0.60 | 0.27 | 10% PDO/MTBE | 0.10 | 80 | 80 | 5 | 59 | 5.12 | 0.87 | 0.41 |

Promoter = Na-acetate
Ligand = B9PBN-2
THF = tetrahydrofuran
TBA = t-butanol
MTBE = methyl=t=butyl ether
DPE = diphenylether
16* & 35* = anomalous

TABLE 2

Dilute Ligand Comparison of Self-Assembly vs. Stepwise Preform Methods

| EX | Ligand | Pre-Form | Pro-Moter | Co Wt % | Atom Ru/Co | Bidentate Ligand L/Ru | Co: | Ru: | L: | R$_x$ Time Hrs. | MADE PDO + HPA % | HPA → PDO Conv | G/L/h | PDO Wt % | HPA Wt % |
|---|---|---|---|---|---|---|---|---|---|---|---|---|---|---|---|
| 43 | BDIBPE | Step | NaOAc | 0.2 | 0.4 | 0.385 | 2.00 | 0.80 | 0.31 | 3 | 10.34 | 0.49 | 25.50 | 5.014 | 5.322 |
| 44 | B9PBN-2 | Step | NaOAc | 0.2 | 0.4 | 0.385 | 2.00 | 0.80 | 0.31 | 1 | 6.91 | 0.70 | 51.13 | 4.867 | 2.043 |
| 45 | BDIBPE | Self | NaOAc | 0.1 | 0.4 | 0.385 | 2.00 | 0.80 | 0.31 | 3 | 11.29 | 0.63 | 27.85 | 7.138 | 4.151 |
| 46 | B9PBN-2 | Self | NaOAc | 0.1 | 0.4 | 0.385 | 2.00 | 0.80 | 0.31 | 4 | 13.67 | 0.78 | 25.29 | 10.66 | 3.008 |

BDIBPE = 1,2-bis(di-isobutylphosphino)ethane
Self = Co/Ru/P preformed together
Step = preform of phosphine ligand with ruthenium carbonyl, followed by addition of dicobaltoctacarbonyl
G/L/h = reaction rate expressed as grams of PDO + HPA formed per liter of liquid volume per hour.

Water Extraction

The water extraction should be done at a reduced temperature relative to the reaction step, and under CO pressure, to suppress degradation of metal carbonyl catalyst. For the current batch experiments, this was accomplished via cooling the reaction mixture to 45° C. or lower. The desired amount of water (typically ⅕ to ⅒ of the reaction mass to effect concentration of product) was then added to a small cylinder connected to the top of the reactor and "blowcased" into the reactor via application of syngas pressure. Extraction was accomplished via stirring the water/solvent mixture (two immiscible liquid phases) using the same autoclave agitator as that used to mix and disperse syngas during reaction. After stirring for 0.5 to 1.0 hours, the entire mixture was transported to a separator assembly comprising a pressure cylinder (500-ml) with a bottom sight glass sized such that the bottom 10 to 75 milliliters of sample would be visible to allow visual discernment of the interface between solvent and aqueous product phases. The separator assembly was maintained at a temperature below 45° C. and at a pressure of at least 3 MPa of 2:1 syngas (minimum 1 MPa CO partial pressure). Under these conditions, no decomposition of metal carbonyl catalyst was observed. Aqueous product and solvent phase could thus be separated.

The separator apparatus was equipped with a bottom drain valve to allow draining of all aqueous products (typically 10 to 40 grams) into a sample vessel. The remaining solvent and catalyst could then be pressured back into the autoclave reactor, to effect a second reaction cycle, taking into account the loss of solvent and catalyst due to sampling during reaction. Five or more cycles could be effected before cumulative loss of solvent and catalyst prevented further examination. Optionally, additional solvent could be added to allow the recycles to proceed at a diluted catalyst concentration.

EXAMPLES 47–52

A series of batch experiments was conducted to demonstrate the viability of water recycle to recover product and recycle of one-step catalyst with a non-water-miscible solvent phase.

The reactor mixture comprised 133.5 grams of methyl-tert-butyl ether (MTBE) and 14.8 grams of ethanol as solvent. To this was added 2.0 grams of cobalt 2-ethylhexanoate ("cobalt octoate") at 16.5% cobalt metal content, 0.54 grams of triruthenium dodecacarbonyl, 1.50 grams of "B9PBN-2" bidentate phosphine, 0.4 grams of dimethyldodecylamine promoter, 0.1 grams of triethylphosphine oxide (marker for nmr characterization of phosphine ligand), and 1.0 grams of toluene (organic marker for reaction species). The mixture was charged to 1500 psi (10.3 MPa) with 4:1 H$_2$/CO and heated to 135° C. to preform active catalyst.

The reactor mixture was cooled to 90° C. and 12.0 grams of ethylene oxide (EO) were added to initiate reaction. The reaction was allowed to proceed until gas uptake stopped, indicating virtually complete conversion of EO. An additional 10.4 grams of EO was added for a second reaction phase. After gas uptake again diminished, the reactor contents were cooled to ambient temperature (<30° C.) and 25.2 grams of deionized water were added to extract product under 3 MPa of syngas. After 15 minutes, the extracted mixture was transferred to the sight glass/separator (under syngas pressure) and allowed to phase separate. The resulting product layer (29.3 grams) was drained from the separator.

The remaining upper layer was transferred back to the reactor and reheated to 90° C. under 4:1 syngas. EO was again introduced to initiate a second reaction cycle. This process was continued through 6 cycles, with results shown in Table 3:

TABLE 3

One Step Recycle Reaction Studies with Water Extraction: 90° C.

| Reaction # | Catalyst Dilution | Reaction Hours | Cumulative Reaction Hours | Total HPA=PDO Formed Grams | Yield of PDO/EO | Reaction Rate g/L/h Adj. to 0.2 w % Co | HPA→PDO Conver-Sion | Extract UL PDO Wt % | Extract LL PDO Wt % |
|---|---|---|---|---|---|---|---|---|---|
| 1 | 1.00 | 3 | 3 | 12.59 | 0.72 | 30.42 | 0.99 | 3.7 | 28.9 |
| 2 | 0.87 | 6 | 9 | 19.92 | 0.98 | 24.84 | 0.99 | 3.5 | 34.4 |
| 3 | 0.75 | 6 | 15 | 15.00 | 1.02 | 27.04 | 0.98 | 3.1 | 29.4 |
| 4 | 0.63 | 6 | 21 | 13.87 | 0.88 | 32.37 | 0.97 | 2.5 | 26.0 |
| 5 | 0.52 | 9.5 | 30.5 | 15.30 | 0.97 | 33.78 | 0.98 | 3.0 | 31.8 |
| 6 | 0.41 | 6 | 36.5 | 11.42 | 0.73 | 59.09 | 0.96 | 2.0 | 24.5 |

Key
Reaction rate = grams of PDO formed per liter of liquid volume per hour.
UL = upper solvent layer
LL = lower aqueous layer While the net yield of PDO from EO reflects both reaction selectivity and extraction efficiency for a given cycle, an average molar yield of 88% was obtained. Some catalyst was lost each extraction to the water phase, but the overall reaction rates per mole of cobalt remained nearly constant. The PDO product strongly partitioned into the water phase, whereas the catalyst preferentially remained with the upper solvent phase (see Table 4, below). Importantly, the conversion of 3-HPA to PDO remained high for all cycles, indicating effective recycle of the hydrogenation catalyst component needed to effect a "one-step" synthesis. Table 4 shows the analysis of catalyst components leached into aqueous product for a number of the cycles:

TABLE 4

| Cycle # | Phase | Co ppm | Ru ppm | P ppm |
|---|---|---|---|---|
| 0 | UL | 2145 | 1650 | 1950 |
| 1 | LL | 1100 | 1600 | 1600 |
| 3 | LL | 41 | 50 | 200 |
| 6 | LL | 71 | 6.4 | 65 |
| 6 | UL | 800 | 300 | 1000 |

LL = lower aqueous layer
UL = upper solvent layer

Significant amounts of catalyst components were lost with the first water extraction. This was consistent with visibly poor separation ("rag" layer). However, given the small ratio of aqueous phase solvent (1:7 $H_2O$/solvent extraction ratio), this did not result in significant loss of catalyst. Subsequent reaction cycles and extractions produced clean aqueous/organic phase separations with efficient recovery of PDO (Table 3) but low losses of catalyst components (Table 4). The final upper solvent layer was analyzed at the end of reaction. The analysis shows retention of a substantial portion of the original catalyst and a favorable partition coefficient for all components (Co, Ru, and P) relative to the aqueous phase.

Significance:
Recycle one-step reaction experiments demonstrate an ability to effect a primary separation of catalyst and product via water extraction. A majority of product is extracted into the water phase, while a majority of catalyst in active form is retained in the upper solvent phase and which can be recycled back to the reaction.

Liquid extraction does not entail thermal stress of high cost catalyst components and hence is an advantageous method for recycle of catalyst during commercial production of high boiling products such as 1,3-propanediol.

We claim:
1. A process for producing aliphatic 1,3-diols which comprises:
   a) Contacting at a temperature within the range from about 30 to about 150° C. and a pressure within the range of about 3 to about 25 MPa, an oxirane, carbon monoxide, and hydrogen, in an essentially non-water-miscible solvent in the presence of an effective amount of a homogeneous bimetallic hydroformylation catalyst comprising a cobalt carbonyl compound and a cocatalyst metal which is selected from the group consisting of ruthenium, copper, platinum, and palladium, and which is ligated with a ligand selected from the group consisting of a phosphine ligand, a bidentate or multidentate N-heterocyclic ligand, a porphorine ligand, and a phospholanoalkane ligand, optionally in the presence of a promoter, wherein the molar ratio of ligand to cocatalyst metal atom is in the range of about 0.2:1.0 to about 0.6:1.0, under reaction conditions effective to produce a reaction product mixture containing an aliphatic 1,3-diol;
   b) Adding an aqueous liquid to said reaction product mixture and extracting into said aqueous liquid a major portion of the aliphatic 1,3-diol at a temperature less than about 100° C. to provide an aqueous phase comprising the aliphatic 1,3-diol in greater concentration than the concentration of the aliphatic 1,3-diol in the reaction product mixture and an organic phase comprising at least a portion of the bimetallic hydroformylation catalyst;
   c) Separating the aqueous phase from the organic phase; and
   d) Optionally returning at least a portion of the organic phase containing catalyst to step (a).
2. The process of claim 1 wherein the cobalt carbonyl compound is an essentially nonligated cobalt carbonyl compound.

3. The process of claim 1 wherein the oxirane is ethylene oxide.

4. The process of claim 1 wherein the aqueous liquid is water.

5. The process of claim 1 wherein the aliphatic 1,3-diol is 1,3-propanediol.

6. The process of claim 1 wherein the extraction of step (b) is carried out at a temperature of about 5 to about 90° C.

7. The process of claim 6 wherein the extraction is carried out at a temperature of about 25 to about 55° C.

8. The process of claim 1 wherein the extraction is carried out under carbon monoxide atmosphere.

9. The process of claim 8 wherein the extraction is carried out under about 0.3 to about 5 MPa of carbon monoxide at about 25 to about about 55° C.

10. The process of claim 1 wherein the oxirane concentration is not less than about 0.2% by weight.

11. The process of claim 10 wherein the oxirane concentration is from about 0.2 to about 20% by weight.

12. The process of claim 11 wherein the oxirane concentration is from about 0.2 to about 10% by weight.

13. The process of claim 1 wherein the temperature in step (a) is in the range of about 50 to about 125° C.

14. The process of claim 13 wherein the temperature is in the range of about 60 to about 110° C.

15. The process of claim 1 wherein the pressure in step (a) is in the range of about 5 to about 15 MPa.

16. The process of claim 15 wherein the pressure is in the range of about 7 to about 12 MPa.

17. The process of claim 1 wherein the cocatalyst metal is ruthenium.

18. The process of claim 1 wherein solvent is selected from the group consisting of alcohols and ethers described by the formula:

where $R_1$ is hydrogen or $C_{1-20}$ linear, branched, cyclic, or aromatic hydrocarbyl or mono- or polyalkylene oxide and $R_2$ is $C_{1-20}$ linear, branched, cyclic or aromatic hydrocarbyl, alkoxy or mono- or polyalkylene oxide.

19. The process of claim 1 wherein the solvent is selected from the group consisting of solvents described by the formula:

wherein $R_1$ is hydrogen or $C_{1-8}$ hydrocarbyl and $R_3$, $R_4$, and $R_5$ are independently selected from $C_{1-8}$ hydrocarbyl, alkoxy, or alkylene oxide.

20. The process of claim 1 wherein the solvent is selected from the group consisting of methyl-t-butyl ether, ethyl-t-butyl ether, diethyl ether, phenylisobutyl ether, ethoxyethyl ether, diphenyl ether, and diisopropyl ether.

21. The process of claim 1 wherein the phosphine ligand is a ditertiary phosphine ligand.

22. The process of claim 21 wherein the ditertiary phosphine ligand is selected from the group consisting of phosphines of the general formula:

wherein each group R and R' independently or jointly is a hydrocarbon moiety of up to 30 carbon atoms, and Q is an organic bridging group of 2 to 4 atoms in length.

23. The process of claim 1 wherein the ligand is a N-heterocycle selected from the group consisting of 2,2'-dipyridyl, 2,2'-bipyrimidine, and 2,4,6-tripyridyl-s-triazine.

24. The process of claim 1 wherein the ligand is a phospholanoalkane selected from the group consisting of 1,2-bis [(2R, 5R)-2,5-dimethylphospholano]ethane, 1,2-bis [(2S, 5S)-2,5-dimethylphospholano]ethane, a racemic mixture of the two, and 1,2 bis (phospholano) ethane.

25. The process of claim 1 wherein the ligand is a porphorine selected from the group consisting of octaethylporphorines and tetraphenylporphorines.

26. The process of claim 1 wherein the ligand to cocatalyst metal molar ratio is in the range of about 0.20:1.0 to about 0.40:1.0.

27. The process of claim 1 wherein a promoter is used and it is lipophilic.

28. The process of claim 27 wherein the lipophilic promoter is selected from the group consisting of quaternary ammonium or phosphonium salts, lipophilic amines, lipophilic arsines, and lipophilic phosphine oxides.

29. The process of claim 1 further comprising extracting residual catalyst from the aqueous phase and returning said residual catalyst to step (a).

30. The process of claim 1 wherein at least a portion of the organic phase containing catalyst is returned to step (a).

31. The process of claim 1 wherein the cocatalyst metal to cobalt molar ratio is at least about 0.05:1.

32. The process of claim 31 wherein the cocatalyst metal to cobalt molar ratio is from about 1:1 to about 1:2.

* * * * *